(12) United States Patent
Leitold et al.

(10) Patent No.: US 10,772,680 B2
(45) Date of Patent: Sep. 15, 2020

(54) GOLD-BASED ABLATION ELECTRODE AND METHOD

(71) Applicant: Heraeus Deutschland GmbH & Co. KG, Hanau (DE)

(72) Inventors: Christiane Leitold, Wölfersheim (DE); Thorsten Keller, Darmstadt (DE); Lydia Buckow, Erlensee (DE); Christian Hammermeister, Bruchköbel (DE); Winfried Krämer, Bad Orb (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 421 days.

(21) Appl. No.: 15/650,767

(22) Filed: Jul. 14, 2017

(65) Prior Publication Data

US 2018/0014881 A1    Jan. 18, 2018

(30) Foreign Application Priority Data

Jul. 15, 2016 (EP) .................................... 16179717

(51) Int. Cl.
*C22C 5/02* (2006.01)
*A61B 18/14* (2006.01)
*C25B 11/04* (2006.01)
*A61B 18/00* (2006.01)

(52) U.S. Cl.
CPC ............ *A61B 18/1492* (2013.01); *C22C 5/02* (2013.01); *C25B 11/0473* (2013.01); *A61B 2018/00005* (2013.01); *A61B 2018/00577* (2013.01); *A61B 2018/1405* (2013.01); *A61B 2562/0209* (2013.01)

(58) Field of Classification Search
CPC .............................. C22C 5/02; C25B 11/0473
See application file for complete search history.

(56) References Cited

U.S. PATENT DOCUMENTS

| | | | |
|---|---|---|---|
| 2,164,938 A * | 7/1939 | Peterson | C22C 5/02 420/496 |
| 5,348,554 A | 9/1994 | Imran et al. | |
| 6,099,524 A | 8/2000 | Lipson et al. | |
| 9,089,339 B2 * | 7/2015 | McDaniel | A61B 18/1492 |

* cited by examiner

*Primary Examiner* — Jessee R Roe
(74) *Attorney, Agent, or Firm* — Dicke, Billig & Czaja, PLLC

(57) ABSTRACT

One aspect relates to an ablation electrode for high-frequency ablation in medical technology, whereby the ablation electrode includes a gold alloy. One aspect relates to a catheter tip for use with a catheter device, including an ablation electrode, as well as a catheter device for high-frequency ablation, including a catheter tip, as well as the use of an ablation electrode, a catheter tip or a catheter device for high-frequency ablation; as well as a process for production of an ablation electrode.

14 Claims, 4 Drawing Sheets

102 a)

301 b)

302

303

GOLD-BASED ABLATION ELECTRODE AND METHOD

CROSS-REFERENCE TO RELATED APPLICATIONS

This Utility Patent Application claims priority to European Patent Application No. EP 16179717.0, filed on Jul. 15, 2016, which is incorporated herein by reference.

BACKGROUND

One aspect relates to an ablation electrode for high-frequency ablation in medical technology, whereby the ablation electrode includes a gold alloy. One aspect relates to a catheter tip for use with a catheter device, including an ablation electrode, as well as a catheter device for high-frequency ablation, including a catheter tip, as well as the use of an ablation electrode, a catheter tip or a catheter device for high-frequency ablation; as well as a process for production of an ablation electrode.

In catheter ablations, tissue emitting incorrect electrical pulses is specifically eliminated or scars are caused in tissue areas to interrupt the conduction of the incorrect pulses. In high frequency ablation, a catheter is introduced into the tissue and locally limited destruction by heat is caused by the heat developed by an applied high-frequency current. The destruction originates from an ablation electrode that is situated at the tip of the distal end of a catheter device. The heat is usually generated in the electrode by high-frequency waves with a frequency above 1 kHz. To assure sufficient heat dissipation during the treatment of the patient, catheter components often need to be optimised, through extensive design efforts, for sufficient heat dissipation, for example by means of cooling channels. U.S. Pat. No. 5,348,554 describes an ablation electrode designed to have an internal cooling for improved heat dissipation, because the component itself does not provide for sufficient heat dissipation.

Platinum-iridium alloys that are in general use in medical technology, in some cases palladium alloys as well, are used as electrode materials. With regard to catheter devices without cooling or catheter devices with passive cooling, it would be desirable to have alloys with a higher thermal conductivity than the aforementioned alloys.

U.S. Pat. No. 6,099,524 describes mapping and ablation catheter systems with electrodes based on gold, gold alloys, platinum, titanium, tungsten, stainless steel, and cobalt-based biocompatible materials. A gold-nickel alloy is specified therein, for example a gold-nickel alloy including 88% by weight gold and 12% by weight nickel. The alloy is said to comprise a higher thermal conductivity than platinum alloys and is therefore used as a heat-dissipating material at the catheter tip of an ablation catheter.

Alloys, such as AuNi12 or other gold-nickel alloys, attain their strength only by the process of solid solution strengthening. As a result, the alloys comprise heat conductivities that do not reach, or only minimally exceed, the thermal conductivity of pure platinum of 74 W/m*K. Other effective solidification mechanisms, such as precipitation hardening, are not known for the AuNi alloy system. As a result, it is not feasible to attain high mechanical strengths based on AuNi alloy systems.

Pure gold has a specific thermal conductivity of 320 W/m*K, but is difficult to process by means of cutting processes, such as turning, milling, and grinding, because its hardness is low. Ablative or erosive procedures, such as laser processing, usually require a holding device, which also is associated with problems related to the attachment to said holding devices in the case of soft materials like gold. As a result, it is not feasible to produce large quantities of ablation electrodes with thin walls on the basis of pure gold by means of these and similar processes in an economically reasonable manner.

But materials with a thermal conductivity as high as that of gold are desirable for application in ablation devices, for example, those with electrodes of low wall thickness, because the high thermal conductivity allows for effective heat dissipation even in the absence of active cooling. In addition, ablation electrodes with thin walls are desirable considering the ongoing trend towards miniaturisation in medical technology.

In general, embodiments overcome the aforementioned disadvantages, at least in part. Specifically, embodiments provide an ablation electrode that includes a high specific thermal conductivity and contains a material that can be produced and processed by means of cutting or erosive processes to have thin walls.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
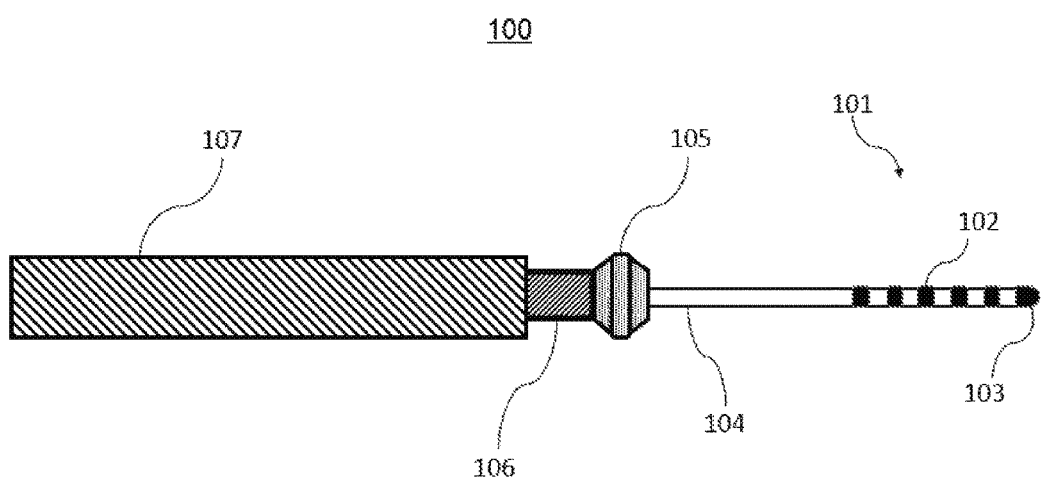
FIG. 1 illustrates a top view of a catheter device including a catheter tip with multiple ablation electrodes.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments is defined by the appended claims.

It is to be understood that the features of the various exemplary embodiments described herein may be combined with each other, unless specifically noted otherwise.

One aspect is an ablation electrode for high-frequency ablation in medical technology, whereby the ablation electrode includes a gold alloy. One aspect provides the gold alloy to be precipitation hardened, to comprise at least 80% by weight gold, and to comprise 1% by weight to 9% by weight cobalt.

Pure gold has a high specific electrical conductivity and a high specific thermal conductivity, but is too soft for the manufacture of ablation electrodes with thin walls. The strength of gold alloys based on pure solid solutions is often insufficient. Although the strength increases with the fraction of the corresponding alloying element, the electrical conductivity and thermal conductivity usually decreases proportionally. The precipitation hardened alloy according to one embodiment includes precipitates that provide for a more effective solidification than pure formations of solid solutions. Simultaneously, it has been found, surprisingly, that the ablation electrode according to one embodiment also includes high electrical conductivity and thermal conductivity. Presumably, the precipitation hardened gold alloy includes a low content of alloying elements, for example, cobalt, in its matrix. Accordingly, cobalt becomes enriched in the precipitates. The high fraction of gold in the matrix presumably has a positive effect concerning the aforementioned properties.

In one embodiment of the ablation electrode, the gold alloy includes 1% by weight to 9% by weight cobalt and at least 90% by weight gold. For example, the gold alloy includes 91% by weight to 99% by weight gold, in one embodiment 92% by weight to 98% by weight gold, in one embodiment 94% by weight to 96% by weight gold and further embodiment 95% by weight gold. In one embodiment, the gold alloy consists of 95% by weight gold and 5% by weight cobalt. Other inevitable impurities, in small amounts, for example, of further metals or elements such as N, O or S, can be a component of the alloy.

A large number and/or large quantity of further alloying elements impairs the electrical conductivity and thermal conductivity of the gold alloy, as a matter of principle. Therefore, gold alloys having a binary composition, for example, gold alloys containing gold and cobalt exclusively, are some embodiments.

In one embodiment of the ablation electrode, the gold alloy includes 2% by weight to 8% by weight cobalt, for example, the gold alloy includes 4% by weight to 6% by weight cobalt, and in one embodiment the gold alloy includes 5% by weight cobalt.

In the range of 2 to 8% by weight cobalt, the alloying system has a particularly large precipitate fraction of cobalt phase in the material, which achieves a particularly effective solidification. In the range of 4% by weight to 6% by weight cobalt, the precipitate fraction is so high that a particularly effective solidification combined with a high electrical conductivity and thermal conductivity is attained. Referring to a gold alloy with a cobalt fraction of 5% by weight, the negligible solubility in the gold and cobalt phases, for example, in the temperature range of 400° C. to 500° C., results in a precipitate fraction of cobalt phase in the material of approximately 5% by weight. A fraction of 5% by weight cobalt in the gold alloy is therefore to be seen as a virtually ideal value, and is therefore preferred in one embodiment. In one embodiment, the gold alloy consists of 2 to 8% by weight cobalt, in one embodiment of 4% by weight to 6% by weight cobalt, and in one embodiment of 5% by weight cobalt, and the remaining fraction of the gold alloy in each case is accounted for by gold.

In one embodiment of the ablation electrode, the gold alloy includes at least one further alloying element selected from the group of platinum, iridium, and palladium. In one embodiment, the total quantity of the further alloying elements is less than 10% by weight, in one embodiment less than 5% by weight, and in one embodiment less than 1% by weight.

The aforementioned platinum metals are characterized, for example, by their good biocompatibility, reaction inertness and the associated corrosion resistance as well as their good electrical conductivity and thermal conductivity.

In one embodiment of the ablation electrode, the gold alloy has a specific thermal conductivity of at least 100 W/m*K, in one embodiment of at least 130 W/m*K, and in one embodiment of at least 150 W/m*K. In this context, the gold alloy has a specific thermal conductivity of no more than 200 W/m*K.

High thermal conductivities in excess of 100 W/m*K are advantageous with respect to the application of the electrode as part of an ablation device in that no active or passive cooling element at the catheter tip is required for the dissipation of heat. This reduces the design effort of the ablation device considerably. This simplifies the miniaturisation of the electrode and therefore of the catheter device as well. Moreover, high thermal conductivities are advantageous in some embodiments in that the exposed tissue is destroyed effectively, that is, limited locally to the exposed area. Healthy tissue that is directly adjacent to pathogenic tissue is not needlessly destroyed.

In one embodiment of the ablation electrode, the gold alloy is biocompatible. Specifically, the gold alloy is suitable for direct contact to a eukaryotic tissue.

In one embodiment of the ablation electrode, the gold alloy has a specific electrical conductivity of at least 15 m/Ω*mm$^2$, in one embodiment of at least 19 m/Ω*mm$^2$, in one embodiment of at least 21 m/Ω*mm$^2$. In this context, the gold alloy has a specific electrical conductivity of no more than 28 m/Ω*mm$^2$. In one embodiment of the ablation electrode, the gold alloy has a Vickers hardness HV 1 of at least HV 1=100, in one embodiment of at least HV 1=150, and in one embodiment of at least HV 1=250. In this context, the gold alloy has a Vickers hardness HV 1 of no more than 330.

The ablation electrodes according to one embodiment, if made from gold alloys with the aforementioned Vickers hardness values, are particularly easy to manufacture by means of cutting processes even if they have small geometries, for example, with thin walls. Excessive Vickers hardnesses, for example, of more than HV 1=330 can mean high tool wear and tear, which makes them less preferred.

In one embodiment of the ablation electrode, the gold alloy has a 0.2% yield strength $Rp_{0.2}$ of at least $Rp_{0.2}$=200 MPa, in one embodiment of at least $Rp_{0.2}$=500 MPa. In this context, the gold alloy has a 0.2% yield strength $Rp_{0.2}$ of no more than 700 MPa.

In one embodiment, there is a minimum yield strength in order to prevent plastic deformation of the tool during the processing by cutting. The plastic deformation can be caused either by the tool or by the bracketing of the component. Therefore, ablation electrodes including gold alloys with a minimum 0.2% yield strength of 200 MPas, for example, a minimum 0.2% yield strength of 500 MPa, are preferred in one embodiment. 0.2% yield strengths in excess of 700 MPa can lead to increased tool wear and tear and are therefore less preferred in one embodiment.

In one embodiment of the ablation electrode, the gold alloy includes a tensile strength $R_m$ of at least $R_m$=400 MPa, in one embodiment of at least $R_m$=600 MPa. In this context, the gold alloy includes a tensile strength $R_m$ of no more than 750 MPa.

In one embodiment, it is preferred to have some minimum tensile strength in order to prevent the tool from fracturing due to the pressure during the processing by cutting. Therefore, ablation electrodes including gold alloys with a minimum tensile strength of 400 MPa, for example, a minimum tensile strength of at least 600 MPa, are preferred in one embodiment. Tensile strengths in excess of 750 MPa can lead to increased tool wear and tear and are therefore less preferred in some embodiments.

In one embodiment of the ablation electrode, the elements gold and cobalt form a single-phase solid solution in the gold alloy above 800° C., and the alloy includes a precipitate of meta-stable phases at room temperature and/or at body temperature.

The gold alloy forms a single-phase solid solution at elevated temperature and a second finally distributed precipitate phase upon rapid cooling to room temperature. The phase is also stable at body temperature. Due to the formation of the solid solution being complete at temperatures above 800° C., the formation of precipitates can be controlled in an effective manner, since the cooling is associated with a homogeneous distribution of the individual regions of the precipitates in the structure of the matrix. For this purpose, the material must be rapidly cooled from the solid solution phase (quenched) in order to freeze the voids in the crystal that are present in the solid solution at high temperature. These serve as nucleation centres for the precipitates and allow the precipitate phase to be finely distributed.

In one embodiment, the ablation electrode includes, at least in part, the basic shape of a cylinder, whereby the cylinder is designed, at least over part of its length, as a hollow cylinder, whereby the hollow cylinder has an external diameter D and an internal diameter d.

In one embodiment, the hollow cylinder can be designed appropriately such that (D-d)/2 defines a wall thickness $d_W$, whereby a maximum wall thickness $d_{Wmax}$ is no more than $d_{Wmax}$=2 mm, in one embodiment no more than $d_{Wmax}$=1 mm, in one embodiment no more than $d_{Wmax}$=0.5 mm. In this context, the hollow cylinder preferably has a minimum wall thickness $d_{Wmin}$ of at least 0.08 mm.

In one embodiment, the ablation electrode is designed as a ring electrode, whereby the wall thickness of the ring electrode is as specified above.

In a further embodiment, the ablation electrode includes the basic shape of a semi-sphere, whereby the semi-sphere includes a hollow space. The semi-sphere shell thus formed has an external diameter D and an internal diameter d.

In one embodiment, the semi-sphere shell can be designed appropriately such that (D-d)/2 defines a wall thickness $d_W$, whereby a maximum wall thickness $d_{Wmax}$ is no more than $d_{Wmax}$=2 mm, in one embodiment no more than $d_{Wmax}$=1 mm, in one embodiment no more than $d_{Wmax}$=0.5 mm. In this context, the semi-sphere shell has a minimum wall thickness $d_{Wmin}$ of at least 0.08 mm.

Embodiments that are a combination of hollow cylinder and semi-sphere shell are conceivable as well, for example a semi-sphere shell that is connected to a hollow cylinder cylinder by means of the front faces.

Due to the high thermal conductivity and electrical conductivity of the ablation electrode according to one embodiment, the manufacture of electrodes with low wall thickness of less than 2 mm is feasible, whereby wall thicknesses down to 0.08 mm are technically feasible. The wall thicknesses of the electrode being low contributes to being able to making the diameter of the catheter tip altogether smaller. As a result, entry into areas of blood vessels that are difficult to access can be simplified.

A contribution to meeting at least one of the objects according to one embodiment is made by a catheter tip for use with a catheter device, including an ablation electrode according to any one of the embodiments specified above.

In one embodiment, the ablation electrode is used as part of a catheter tip, which, in turn, is part of a catheter device on the distal end of the device.

In one embodiment of the catheter tip, the ablation electrode includes a first and a second surface, whereby the first surface is connected to an electrically conductive element of the catheter device, at least the second surface includes the gold alloy, and the second surface is intended to contact a biological tissue.

In one embodiment, the ablation electrode includes the basic shape of a cylinder, whereby the cylinder is designed, at least over part of its length, as a hollow cylinder that includes an external diameter D and in internal diameter r, whereby (D-d)/2 defines a wall thickness $d_W$. In one embodiment, the outside of the cylinder and/or hollow cylinder forms, at least in part, the second surface that is intended to contact a biological tissue. In one embodiment, the internal wall of the hollow cylinder forms, at least in part, the first surface that is connected to an electrically conductive element of the catheter device.

In one embodiment, only the external area of the electrode establishing contact to the tissue to be destroyed during the treatment includes the gold alloy according to one embodiment. A different alloy can be used on the inside for transmission of the electrical signals and for heat transport.

In a further embodiment, it is also conceivable that the ablation electrode and/or the catheter tip comprise(s) the gold alloy only in those areas, in which particularly high heat transfer is required.

In one embodiment, the catheter tip includes no further cooling element except for the ablation electrode.

The ablation electrode, as such, can be interpreted to be a cooling element due to its high thermal conductivity, since the ablation electrode does not only transport heat to the tissue, but also dissipates heat from the tissue. Accordingly the catheter tip is free of a cooling element other than the ablation electrode. The cooling element can be an active or a passive cooling element. The overall design layout of the catheter tip is made simpler if no additional active and/or passive cooling elements are incorporated at the catheter tip. A passive cooling element shall be understood to be, for example, a device that allows a coolant to be continuously conveyed through the cooling element. A passive cooling element can, for example, contain a further metallic element with a high thermal conductivity that is not involved in the actual ablation process, that is, does not to transfer any high-frequency energy to the tissue.

A contribution to meeting at least one of the objects according to one embodiment is made by a catheter device for high-frequency ablation, including a catheter tip according to any one of the embodiments specified above.

In one embodiment, the catheter tip according to one embodiment is used as part of a catheter device. In one embodiment, the catheter device is used in high-frequency ablation.

In one embodiment, the catheter device includes an elongated and at least partially flexible catheter body, whereby the catheter body includes a proximal and a distal end and the ablation catheter tip is situated at the distal end of the catheter body.

The actual treatment, that is, the destruction of the pathogenic tissue, takes place at the distal end of the catheter body, whereas the proximal end is connected to the control device of the catheter device.

A contribution to meeting at least one of the objects according to one embodiment is made by the use of an ablation electrode according to any one of the embodiments specified above, the use of a catheter tip according to any one of the embodiments specified above or the use of the catheter device according to any one of the embodiments specified above for high-frequency ablation.

A contribution to meeting at least one of the objects specified above is made by a process for the manufacture of an ablation electrode, whereby the process includes the steps of:
   a. Providing a precursor made of a gold alloy, whereby the gold alloy comprises at least 80% by weight gold and 1% by weight to 9% by weight cobalt;
   b. forming the precursor into a wire-shaped form body;
   c. solution annealing of the form body at a temperature of 800 to 1,000° C. for at least 15 min;
   d. quenching the solution-annealed form body by dipping it into a liquid medium such that the form body is cooled down by more than 500° C.;
   e. precipitation hardening of the quenched form body at a temperature of 200° C. to 600° C. for a period of at least 0.5 h;
   f. forming the precipitation-hardened form body into the ablation electrode.

To achieve a high electrical conductivity and thermal conductivity of the ablation electrode according to one embodiment, it is necessary to subject the gold alloy to a precipitation hardening.

This involves initially, in step a., providing a precursor of the gold alloy having the specified weight fractions of cobalt, for example by melting the starting materials in a continuous casting process by means of an induction furnace, whereby, form bodies with a circular cross-section are obtained.

Subsequently, in step b., the precursor is reformed into a wire-like form body, which can be implemented, for example, by means of multiple drawing dies in multiple drawing stages. The wire-like form bodies thus obtained are then straightened and cut to size.

Subsequently, the form bodies thus obtained are subjected to solution annealing according to step c., whereby, a single-phase alloy with the formation of a homogeneous solid solution is obtained. The duration of solution annealing depends on the size of the workpiece. Usually, the solution annealing takes place for at least 15 min and maximally 3 h. Longer annealing times do not have a disadvantageous effect, though.

During the subsequent quenching of the solution-annealed form body according to step d. and the subsequent precipitation hardening according to step e., the single-phase solid solution transitions into a two-phase alloy.

The quenching according to step d. is performed appropriately such that the form body cools down by at least 500° C. In one embodiment, the form body is cooled down by at least 700° C., and cooling down to room temperature is more preferred in one embodiment.

In order to attain the desired effect of precipitation hardening, that is, in order to attain the advantageous mechanical properties and a high electrical conductivity and thermal conductivity, the subsequent precipitation hardening according to step e. must be performed for at least 0.5 h. Usually, the precipitation hardening is performed for at most 40 h, but longer precipitation hardening times do not necessarily have a disadvantageous effect.

In one embodiment, the procedural steps denoted a. through f. are performed in the specified order.

In one embodiment, the precursor is provided according to step a., followed by steps c. through e. being performed subsequently. After the precipitation hardening according to step e. follows the forming of the precipitation-hardened material into a wire-like form body and then the forming to form the ablation electrode. However, this is feasible only if the forming machines used in this context, for example wire drawing units or rollers can form the material as a result of all the high strength that is achieved by the precipitation annealing without any tears or other production problems occurring.

In one embodiment of the process, the gold alloy includes 1% by weight to 9% by weight cobalt and at least 90% by weight gold.

In one embodiment of the process, the gold alloy includes 2% by weight to 8% by weight cobalt, in one embodiment the gold alloy includes 4% by weight to 6% by weight cobalt, and in one embodiment the gold alloy includes 5% by weight cobalt.

In one embodiment of the process, the solution annealing according to step c. and/or the precipitation hardening according to step e. take place in a reducing atmosphere.

In one embodiment of the process, the solution annealing according to step c. and/or the precipitation hardening according to step e. take place in an inert gas atmosphere.

In one embodiment of the process, the reducing atmosphere contains approximately 95% by volume nitrogen and approximately 5% by volume hydrogen.

Cobalt easily forms the oxides, CoO (cobalt(II) oxide), $Co_2O_3$ (cobalt(III) oxide), and $Co_3O_4$ (cobalt(II,III) oxide). To prevent the oxidation, the solution annealing is implemented in an inert gas atmosphere or in a reducing atmosphere.

In one embodiment of the process, the precipitation hardening according to step e. is implemented for a period of 15 h to 30 h, in one embodiment for a period of 17 h to 30 h, in one embodiment for a period of 24 h to 30 h. Specifically, the duration of the precipitation hardening is 30 h.

With a view to attaining particularly high electrical conductivity and thermal conductivity, it has been evident that the precipitation hardening needs to be implemented for at least 15 h. Particularly good results are obtained with an annealing time of 30 h. Similarly good results are expected for an annealing time in the range between 25 h and 40 h.

In one embodiment of the process, the quenching of the form body after step d. takes place by immersion in a water bath.

The quenching can take place in particularly easy manner, without requiring much equipment, through the use of a water bath.

A contribution to meeting at least one of the objects according to one embodiment is made by a process according to at least one of the preceding embodiments for production of an ablation electrode according to at least one of the preceding embodiments.

In one embodiment refinements of components of any inventive category, for example, of the ablation electrode according to one embodiment, the catheter tip according to one embodiment, the catheter device according to one embodiment, the use according to one embodiment and the process according to one embodiment shall be preferred in the same manner for identically named or corresponding components of any other category according to one embodiment.

Ablation Electrode, Catheter Tip, Catheter Body, Catheter Device

An ablation electrode is a component of a catheter tip. The catheter tip is a component of a catheter body of a catheter device. The catheter body is designed to be flexible, at least at the catheter tip.

The catheter device has a proximal and a distal end. The catheter tip of the catheter device is situated at the distal end.

The catheter body has a proximal and a distal end. The catheter tip of the catheter device is situated at the distal end.

The catheter tip, in turn, includes one or more ablation electrode(s). The ablation electrode or ablation electrodes transport heat energy to the tissue.

Combined with a catheter tip and the ablation electrode or ablation electrodes, the catheter device is well-suited for all conceivable electrophysiological medical applications. This includes, for example, high-frequency ablation. Other conceivable applications are cryoablation and diagnostic applications using mapping catheters. In one embodiment, all materials of the ablation electrode, catheter tip, catheter body, and catheter devices are biocompatible. For example, the ablation electrode consists exclusively of biocompatible metals and/or a biocompatible alloy.

Biocompatible Metal, Biocompatible Alloy

A biocompatible metal and/or a biocompatible alloy is bio-tolerant and/or bio-inert. For example, a metal and/or an alloy can be certified as biocompatible in the sense of ISO 10993 1-20 and is well-suited for direct contact to eukaryotic tissue.

Precipitation of Meta-Stable Phases

In the scope of one embodiment, "precipitation of meta-stable phases", shall be understood to mean that a precipitation, in finally distributed form, proceeded in the elemental solid solution of an alloy. The precipitation is, for example, an impediment to dislocation motions and thus increases the strength. The precipitation of metastable phases is effected, for example, by precipitation hardening.

Room Temperature

In the scope of one embodiment, room temperature shall be understood to be a temperature that is common for a closed room, usually 15° C. to 30° C., in one embodiment 20 to 25° C.

Body Temperature

In the scope of one embodiment, body temperature shall be understood to mean a temperature that is common on the inside of the body at the time of treatment by a catheter ablation of a human or animal body. For example, body temperature shall be understood to be the normal temperature of a healthy human or animal body, whereby this temperature is in the range of 36.3° C. to 37.4° C. Obviously, lower or higher body temperatures are conceivable as well, for example in a case of hypothermia or a disease associated with fever.

Measuring Methods

Specific Electrical Conductivity

The electrical conductivity of the respective materials is determined in accordance with DIN IEC 60468 by means of a four-point measurement on wires. In the measuring set-up, wires with an effective testing length of 240 mm and/or 1,000 mm length are clamped in electrically conductive manner. A constant electrical current of suitable amperage, presently 1,000 mA, is supplied into the wire over a wire length of 400 mm and/or 1,300 mm. The difference in length of current supply and voltage measurement serves for the formation of a uniform current density over the test length. The drop of electrical voltage over the test length is measured. The voltage values thus obtained are used to determine the specific electrical conductivity by means of Ohm's law. The actual wire diameter is determined by means of a micrometer screw. The test length is determined with the clamping device of the wires.

The clamping device is of the type, BURSTER Type 2381 "precision clamping device" for four-pole measurements. A Keithley Multimeter 2000 is used as the voltmeter. A TTi PL310 power supply unit is used as the source of electrical current. During the measurement, the temperature is between 20° C. and 22° C.

Specific Thermal Conductivity

The specific thermal conductivity is determined indirectly by Conversion from the experimentally determined specific electric conductivity using the Wiedemann-Franz law.

Vickers Hardness

The hardness is determined by means of a hardness testing device of the type, VMHT MOT made by Leica according to Vickers in accordance with DIN EN ISO 6507-1. A pyramid-shaped test body is pressed at a defined load perpendicularly into the metallographically polished surface of the material. The hardness is calculated from the cross-section of the impression produced by the test body and the test load. The test load is 1 kg, which leads to the unit being specified as HV 1. During the measurement, the temperature is between 20° C. and 22° C.

0.2% Yield Strength $Rp_{0.2}$ and Tensile Strength $R_m$

The yield strength and the tensile strength are each determined in a elongation-controlled tensile experiment in accordance with DIN ISO 6892-1. A universal testing machine Zwick Roell, type Z250/SN5A is the equipment used in this test. A 200 kN load cell with a measuring range from 0.4 to 240 kN is used as the force measuring facility. A device made by Multisense with a measuring range of 50 mm is used as the elongation change sensor. The sample length of the wire was 200 mm and the clamping length was 100 mm and the effective test length was 50 mm. The test speed was 10 mm per minute. A Zwick 8406 clamping tool was used as the tool for clamping the samples.

Examples

Aspects are illustrated in the following by means of examples and drawings without the examples and drawings limiting the invention in any way or manner. Unless specified otherwise, the drawings are not true to scale.

Inventive Example

Wire-like form bodies that had diameters between 3.0 mm and 3.2 mm and were suitable for the production of inventive ablation electrodes were produced. The mechanical and physical properties were determined by means of the wire-like form bodies. Subsequently, the tested form bodies were processed by means of cutting processes to produce ablation electrodes with a basic wall thickness of 0.29 mm. Additional boreholes were produced in these ablation electrodes. The wall thickness in the area of the depressions produced by the boreholes was 0.16 mm.

Initially, a precursor of a gold alloy with a gold fraction of 95.0% by weight gold and 5.0% by weight cobalt was produced by melting in a continuous casting induction furnace. The starting materials were gold granulate with a purity of 99.99% by weight and pieces of cobalt with a purity of 99.9% by weight. The gold granulate and the pieces of cobalt were pre-melted in a 2,400 g batch in a clay crucible in a carbon monoxide atmosphere. Then, the molten material was decanted into a graphite mould to form ingots with an edge length of 20×20 mm. This was allowed to cool down to room temperature and then the gold-cobalt alloy was remelted at 1,100° C. and decanted in the continuous casting process. As a result, form bodies with a round cross-section, a diameter of 7 mm, and a length of 3,400 mm were obtained. Subsequently, the chemical composition of the gold alloy was analysed by means of glow discharge spectroscopy. The composition thus determined was 95.4% by weight gold and 4.6% by weight cobalt.

The precursor of the gold alloy thus obtained was then reduced from a cross-sectional diameter of 7.0 mm to a nominal diameter of 3.0 mm by wire drawing using a Malmedie single drawing facility with diamond dies. The wire drawing involved multiple intermediate drawing stages, starting from the precursor with 7.0 mm, via 6.00 mm, 5.00 mm, 4.20 mm, 3.70 mm, 3.40 mm, and 3.10 mm to 3.00 mm.'s The drawing rate was 15 m per minute. The wire-like form body thus obtained was straightened and cut into rods with the length of 1,800 mm each. Pieces of wire with an actual diameter between 3.0 mm and 3.20 mm were obtained.

The wire-like form bodies were then subjected to solution annealing. For this purpose, the form bodies were placed in a tube furnace (manufacturer: Carbolite® Gero, maximum temperature: 1200° C.) and annealed for one hour at 950° C. in forming gas (composition: 95% by volume nitrogen, 5% by volume hydrogen). The form bodies were removed from the hot furnace and then immediately quenched by dipping into a water basin.

Subsequently, a precipitation annealing at 400° C. was performed in forming gas for each form body to be tested using the aforementioned tube furnace for the precipitation hardening. According to example 1, the precipitation annealing was performed for a period of 10 h. According to example 2, the precipitation annealing was performed for a period of 17 h. According to example 3, the precipitation annealing was performed for a period of 24 h, and according to example 4, the precipitation annealing was performed for 30 h.

Non-Inventive Reference Examples

Wire-like form bodies with a cross-sectional diameter ranging from 3.0 to 3.2 mm, as in the examples, were used as reference examples.

A wire-like form body made of a gold alloy with a fraction of 95% by weight gold and 5% by weight cobalt that was not subjected to precipitation annealing and therefore was not subjected to a precipitation hardening was tested as reference example 1. A gold alloy with a fraction of 99% by weight gold and 1% by weight titanium was tested as reference example 2. The alloying system is amenable to precipitation hardening and was subjected to a precipitation annealing or 1 h at 550° C. For this system, the maximum hardness was obtained in the experiments at 1 h annealing time (precipitation annealing). A wire-like form body made of pure gold was tested as reference example 3. A gold alloy with a fraction of 90% by weight gold and 10% by weight platinum was tested as reference example 4. A platinum-iridium alloy with a fraction of 90% by weight platinum and 10% by weight iridium was tested as reference example 5. A palladium-platinum alloy with a fraction of 80% by weight palladium and 20% by weight platinum was tested as reference example 6. The alloying systems of reference examples 4 to 6 are not amenable to precipitation hardening and were therefore not subjected to a precipitation annealing.

Analysis

The examples of the table below illustrate the thermal conductivity and electrical conductivity of the form bodies of examples 1 to 4 obtained by precipitation hardening in a comparison to non-inventive reference examples. The time in hours specified for the inventive foreign bodies made of AuCo5 is the duration of the precipitation annealing and therefore the duration of the precipitation hardening.

| Example no. | Composition form body | Thermal conductivity/ (W/m*K) | Electrical conductivity/ (m/Ω*mm$^2$) |
|---|---|---|---|
| Example 1 | AuCo5, 10 h | 110.2 | 15.2 |
| Example 2 | AuCo5, 17 h | 142.9 | 19.7 |
| Example 3 | AuCo5, 24 h | 142.0 | 19.6 |
| Example 4 | AuCo5, 30 h | 156.4 | 21.6 |
| Reference example 1 | AuCo5 | 14.0 | 1.9 |
| Reference example 2 | AuTi1 | 30.0 | 4.2 |
| Reference example 3 | Au (99.99 wt. %) | 317.5 | 43.9 |
| Reference example 4 | AuPt10 | 72.5 | 10.0 |
| Reference example 5 | PtIr10 | 29.0 | 4.0 |
| Reference example 6 | PdPt20 | 36.3 | 5.0 |

The table evidences the improved thermal conductivity and electrical conductivity of precipitation-hardened AuCo5 form bodies as compared to form bodies made from conventional alloys on the basis of AuPt, PtIr, and PdPt that cannot be subjected to precipitation hardening. Moreover, the beneficial effect of precipitation hardening as compared to an AuCo5 alloy that was not subjected to precipitation hardening is demonstrated. In addition, the table above illustrates the clearly higher thermal conductivity and electrical conductivity of precipitation-hardened form bodies based on gold-cobalt as compared to precipitation-hardened form bodies based on gold-titanium.

The improved mechanical properties of the form bodies produced on the basis of AuCo5 as compared to form bodies produced, for example, on the basis of pure gold, is illustrated in the table below. The table illustrates the 0.2% yield strength $Rp_{0.2}$, the tensile strength $R_m$, and the Vickers hardness HV 1.

| Example no. | Composition form body | $Rp_{0.2}$/MPa | $R_m$/MPa | HV 1 |
|---|---|---|---|---|
| Example 1 | AuCo5, 10 h | 589 | 663 | 259.6 |
| Example 2 | AuCo5, 17 h | 216 | 469 | 176.0 |
| Example 3 | AuCo5, 24 h | 218 | 504 | 106.3 |
| Example 4 | AuCo5, 30 h | 297 | 434 | 132.3 |
| Reference | AuCo5 | not | not | 142.4 |

-continued

| Example no. | Composition form body | $R_{p0.2}$/MPa | $R_m$/MPa | HV 1 |
|---|---|---|---|---|
| example 1 | | determined | determined | |
| Reference example 2 | AuTi1 | 430 | 559 | 171.9 |
| Reference example 3 | Au (99.99 wt. %) | 217 | 221 | 75.7 |
| Reference example 4 | AuPt10 | 409 | 451 | not determined |
| Reference example 5 | PtIr10 | 600 | 640 | 200 |
| Reference example 6 | PdPt20 | 545 | 578 | 60 |

Specifically the AuCo5 alloy precipitation-hardened for 10 h showed good mechanical properties in terms of its yield strength and tensile strength. Where the mechanical parameters of the precipitation-hardened AuCo5 are comparable to the non-precipitation-hardened alloying systems AuPt5, AuPt10, PtIr10, and PdPt20, the table above indicates that better conductivities are attained. Accordingly, for example, AuPt10 illustrates better properties with respect to the yield strength as compared to AuCo5 precipitation hardened for 17 h or more, but the conductivities are clearly lower.

In summary, it can therefore be concluded that ablation electrodes made of precipitation-hardened gold-cobalt alloy of the inventive composition include optimal properties in terms of the combination of the parameters electrical and thermal conductivity, yield strength, tensile strength, and hardness, and are therefore better suited for ablation applications and at the same time are easier to manufacture than conventional alloys based on AuPt, PtIr, PdPt or pure gold.

Production of Tip Electrodes from AuCo5

Suitable tip electrodes 103 for ablation applications were produced based on the tested form bodies. For this purpose, wire pieces with a cross-sectional diameter of 3.0 mm and a length of 400 mm were reformed into tip electrodes with a wall thickness of 0.29 mm and/or 0.16 mm in the area of the boreholes. For reforming of the wire into the tip electrode, a multiaxis longitudinal lathe was used and the tip electrode was machined by cutting using corresponding suitable turning and drilling tools.

FIG. 1 illustrates a schematic top view of a catheter device 100 that includes multiple inventive ablation electrodes 102, 103. The ablation electrodes 102, 103 are designed in the form of ring electrodes 102 and tip electrode 103. The overall catheter device 100 is well-suited for ablation applications. The catheter device 100 includes an elongated catheter body 104. The catheter body 104 includes a proximal and a distal end. The proximal end of the catheter body 104 is connected to a thumb rest 105, which, in turn, is connected to a mobile plunger 106. The mobile plunger 106 is connected to a control handle 107. Designed to be flexible, the catheter tip 101 is situated at the distal end of the catheter body 104. Multiple ring electrodes 102 are arranged as ablation electrodes 102, 103 at the catheter tip 101, whereby the ring electrodes 102 surround the catheter body 104 completely. A tip electrode 103 including an internal hollow space is situated at the distal end of the catheter tip 101 as a further ablation electrode 102, 103.

The ring electrodes 102 and the tip electrode 103 are made up of a gold-cobalt alloy with a weight fraction of 95% gold and 5% cobalt. The ring electrodes 102 usually have a length between 3 and 6 mm. The individual ring electrodes 102 each have an equidistant spacing from each other. The distance between the individual ring electrodes 102 each is at least 2 mm, in one embodiment 3 to 4 mm. If the distance is too small, the flexibility of the catheter tip 101 is too low. The tip electrode 103 has a length between 2 and 5 mm. The ring electrodes 102 and the tip electrode 103 have a wall thickness ranging from 0.1 to 0.3 mm. The ring electrodes 102 and the tip electrodes 103 are both bio-inert and biocompatible.

Figure 2:
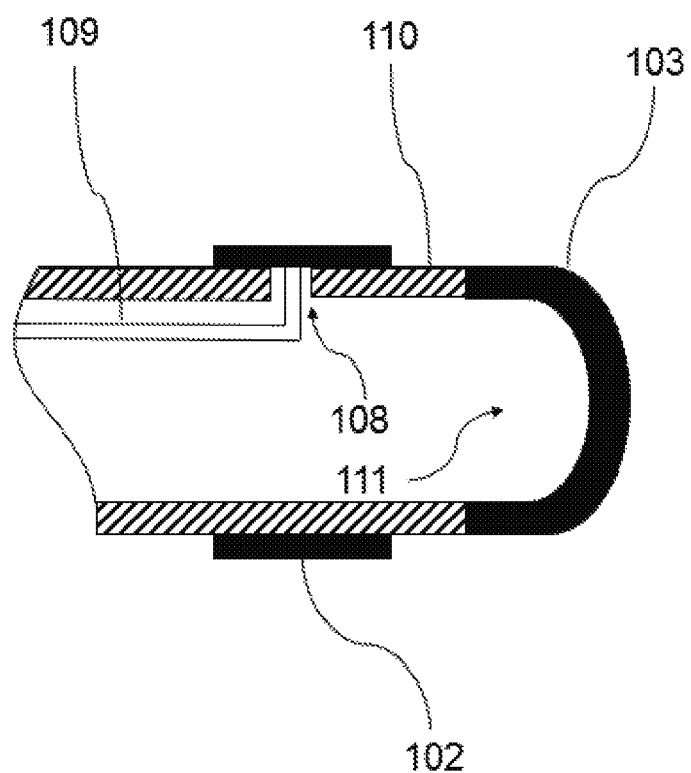
FIG. 2 illustrates a cross-sectional view through a section of a catheter tip.

FIG. 2 illustrates a cross-sectional view through a section of the catheter tip 101. The section including the tip electrode 103 and one ring electrode 102 is illustrated. The tip electrode 103 has an overall semi-spherical shape, includes a hollow space 111 and can be attached to the distal end of the catheter body 104, at the wall 110 thereof, by suitable means, for example by an adhesive (not illustrated). Each of the electrodes 102 and 103 is connected to a separate electrical cable. The figure illustrates the electrical cable 109 that runs through a recess 108 in the wall 110 of the catheter body and establishes electrical contact between the ring electrode 102 and the control unit (not illustrated) of the catheter device 100. The cable 109 is designed in the form of a wire and extends from the ring electrode 102 through the internal space of the catheter body 104 to the control handle 107, and from there to the control unit (not illustrated). In one embodiment, the cable is a wire with a high electrical conductivity, for example a copper wire. The cable 109 transmits the high-frequency energy required for the treatment from the control unit to the ablation electrodes 102, 103, which are designed in the form of ring electrodes 102 and tip electrode 103. The ring electrodes 102 and the tip electrode 103 include a gold alloy with a weight fraction of 95% by weight gold and 5% by weight cobalt. In this context, the surface of the ring electrode 102 and/or tip electrode 103 that faces inward, toward the catheter body 104, can consist of a different alloy, if applicable. In this case, the ring electrodes 102 and/or the tip electrode 103 are made up of two different alloys. The make-up can be attained, for example, by mechanical processing of a core-sheath wire, whereby the core includes a gold-cobalt alloy of inventive composition. In one embodiment, the catheter body 104 includes no active and/or passive cooling facility, that is, is free of cooling elements. Since the thermal conductivity of the ablation electrodes 102, 103, which are designed as ring electrodes 102 and tip electrode 103, is high because of the use of the gold alloy, the heat generated during the treatment is dissipated effectively even in the absence of an active and/or passive cooling facility.

Figure 3:
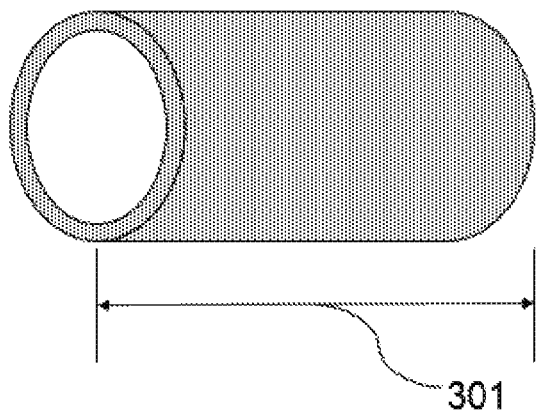
FIG. 3 illustrates a perspective view a) and a cross-sectional view b) through an ablation electrode according to one embodiment, designed as a ring electrode.
Figure 3:
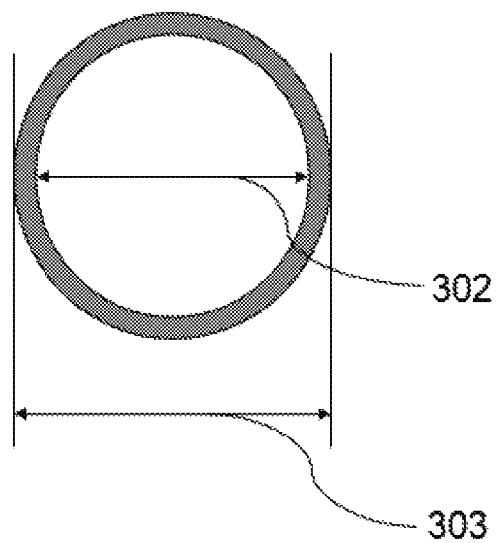

FIG. 3 illustrates an ablation electrode according to one embodiment that is designed as a ring electrode 102 in the present case. FIG. 3 a) illustrates a perspective view of the ring electrode 102. FIG. 3 b) illustrates a cross-sectional view through a ring electrode 102. In general, inventive ablation electrodes 102, 103 can include the basic shape of a cylinder, at least in part, whereby the electrodes are designed in the form of hollow cylinders, at least in part. In the case illustrated, the entire electrode is designed as a hollow cylinder, including ring electrode 102. As illustrated in FIG. 3 a), the ring electrode 102 has a length L 301 that extends from one front face of the hollow cylinder to the corresponding other front face. The length L usually is 3 to 6 mm, though other lengths are possible depending on the individual application. As illustrated in FIG. 3 b), the ring electrode 102 has a circular cross-section with an external diameter D 303 and an internal diameter d 302. The difference between the external diameter D 303 and the internal diameter d 302, divided by two, defines a wall thickness $d_W$ of the ring electrode 102. Ablation electrodes designed according to one embodiment as ring electrodes 102 have a wall thickness $d_W$ of no more than 2 mm. In the case illustrated, the maximum wall thickness $d_{Wmax}$ is equal to 0.3 mm. In addition, the wall of the electrode can include depressions generated by drilling. A minimum wall thickness $d_{Wmin}$ of 80 µm can be produced in these areas. Ablation electrodes 102, 103 made of inventive gold alloys, for example of an AuCo5 alloy, can also have a minimum wall thickness $d_{Wmin}$ of 80 µm across the entire surface of the wall, that is, wall thicknesses this low can be realised by technical means. It is self-evident that the inventive ablation electrodes 102, 103 do not have to have the hollow cylinder or ring shape according to FIG. 3. Aside from others, semi-spherical refinements of electrodes are conceivable, whereby the semi-sphere usually is hollow and therefore is shaped similar to a spherical shell. Electrodes of this type can be used, for example, as tip electrodes 103 in ablation devices 100, since these are closed on one side. Moreover, combinations of the shapes mentioned above are feasible, such as, for example, ablation electrodes 102, 103 shaped as hollow cylinders that are closed on one side. In this context, the closed side can be closed by edges or in rounded manner.

Figure 4:
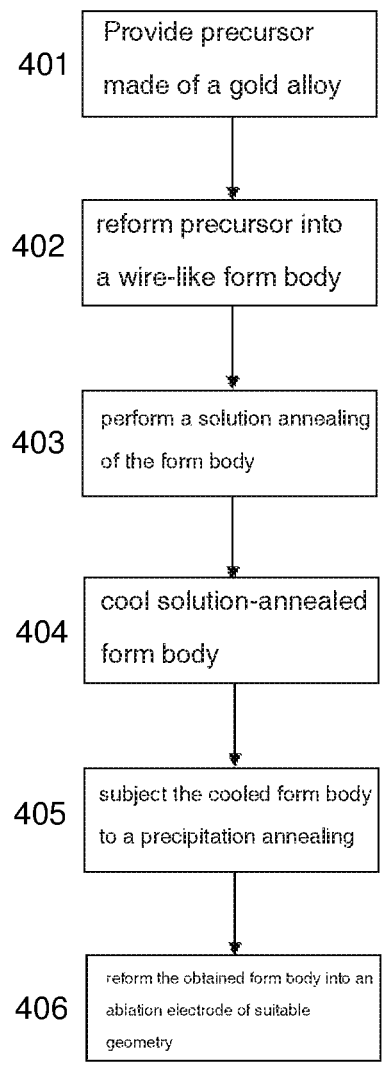
FIG. 4 illustrates a flow diagram for a process according to one embodiment.

FIG. 4 illustrates a flow diagram of an inventive process 400 for the production of an ablation electrode 102, 103, whereby the ablation electrode can be designed, for example, as a ring electrode 102. In a process step a. 401, a precursor made of a gold alloy is provided, whereby the gold alloy includes 95% by weight gold and 5% by weight cobalt. The precursor is designed as a cylinder with a cross-sectional diameter ranging from 6.0 to 10.0 mm and is obtained in a continuous drawing process. In a process step b. 402, the precursor is reformed into a wire-like form body, whereby a form body with a cross-sectional diameter of, for example, 2.0 to 4.0 mm is obtained, depending on the application. In a process step c. 403, a solution annealing of the form body is performed. The solution annealing can be performed, for example, at a temperature of 950° C. for 60 min. In a process step d. 404, the solution-annealed form body is cooled down by more than 500° C. by dipping it into a liquid medium. For example, the solution-annealed form body is quenched from 950° C. to room temperature by dipping it into a water bath. In a process step e. 405, the cooled form body is subjected to a precipitation annealing at a temperature ranging from 200° C. to 600° C. for a period of at least 0.5 h in order to effect the precipitation hardening. For example, the form body including 95% by weight gold and 5% by weight cobalt is annealed for 24 hours at a temperature of 400° C. In a concluding process step f. 406, the form body thus obtained is reformed into an ablation electrode of suitable geometry, for example a ring electrode 102.

Although specific embodiments have been illustrated and described herein, it will be appreciated by those of ordinary skill in the art that a variety of alternate and/or equivalent implementations may be substituted for the specific embodiments illustrates and described without departing from the scope of the present embodiments. This application is intended to cover any adaptations or variations of the specific embodiments discussed herein. Therefore, it is intended that this invention be limited only by the claims and the equivalents thereof.

What is claimed is:

1. An ablation electrode for high-frequency ablation above 1 kHz in medical technology:
   wherein the ablation electrode comprises a gold alloy;
   characterized in that the gold alloy is precipitation-hardened, comprises at least 90% by weight gold, and 1% by weight to 9% by weight cobalt.

2. The ablation electrode of claim 1, characterized in that the gold alloy comprises 2% by weight to 8% by weight cobalt.

3. The ablation electrode of claim 1, characterized in that the gold alloy comprises 4% by weight to 6% by weight cobalt.

4. The ablation electrode of claim 1, characterized in that the gold alloy has a specific thermal conductivity of at least 150 W/m*K.

5. The ablation electrode of claim 1, characterized in that the gold alloy comprises a 0.2% yield strength Rp0.2 of at least Rp0.2=200 MPa.

6. The ablation electrode of claim 1, characterized in that the gold alloy comprises a 0.2% yield strength Rp0.2 of at least Rp0.2=500 MPa.

7. The ablation electrode of claim 1, characterized in that the gold alloy comprises a tensile strength Rm of at least Rm=600 MPa.

8. The ablation electrode of claim 1, characterized in that the elements gold and cobalt form a single-phase solid solution in the gold alloy above 800° C. and in that the alloy comprises a precipitate of metastable phases at room temperature and/or body temperature.

9. The ablation electrode of claim 1, characterized in that the ablation electrode comprises the basic shape of a cylinder, whereby the cylinder is designed, at least over part of its length, as a hollow cylinder, whereby the hollow cylinder has an external diameter D and an internal diameter d, whereby (D-d)/2 defines a wall thickness dW, whereby a maximum wall thickness dWmax is no more than dWmax=2 mm.

10. The ablation electrode of claim 1, characterized in that the ablation electrode comprises the basic shape of a cylinder, whereby the cylinder is designed, at least over part of its length, as a hollow cylinder, whereby the hollow cylinder has an external diameter D and an internal diameter d, whereby (D-d)/2 defines a wall thickness dW, whereby a maximum wall thickness dWmax is no more than dWmax=0.5 mm.

11. The ablation electrode of claim 1 configured for high-frequency ablation above 1 kHz.

12. A catheter tip for use with a catheter device comprising:
   an ablation electrode;
   wherein the ablation electrode comprises a gold alloy;
   characterized in that the gold alloy is precipitation-hardened, comprises at least 90% by weight gold, and 1% by weight to 9% by weight cobalt.

13. The catheter tip of claim 12, characterized in that the catheter tip comprises no further cooling element except for the ablation electrode.

14. A catheter device for high-frequency ablation above 1 kHz, comprising the catheter tip of claim 12.

* * * * *